(12) United States Patent
Fuentes et al.

(10) Patent No.: US 8,652,231 B2
(45) Date of Patent: Feb. 18, 2014

(54) METAL COMPLEXES; USE THEREOF FOR THE PREPARATION OF COMPOSITIONS FOR AGRICULTURAL USE

(75) Inventors: Marta Fuentes, Jerez De La Frontera (ES); Roberto Baigorri, Huarte/Uharte (ES); Eva Bacaicoa, Pamplona (ES); Jose Maria Garcia-Mina, Iza (ES); Jean-Claude Yvin, Saint-Malo (FR)

(73) Assignee: Timac Argo International, Saint-Malo (FR)

( * ) Notice: Subject to any disclaimer, the term of this patent is extended or adjusted under 35 U.S.C. 154(b) by 287 days.

(21) Appl. No.: 13/124,303

(22) PCT Filed: Oct. 15, 2009

(86) PCT No.: PCT/FR2009/051965
§ 371 (c)(1),
(2), (4) Date: May 12, 2011

(87) PCT Pub. No.: WO2010/043819
PCT Pub. Date: Apr. 22, 2010

(65) Prior Publication Data
US 2011/0239717 A1      Oct. 6, 2011

(30) Foreign Application Priority Data

Oct. 15, 2008    (FR) .................................... 08 56977

(51) Int. Cl.
| | | |
|---|---|---|
| *C05D 9/02* | (2006.01) |
| *C07F 13/00* | (2006.01) |
| *C07F 11/00* | (2006.01) |
| *C07F 3/06* | (2006.01) |
| *C07F 15/02* | (2006.01) |
| *C07F 15/04* | (2006.01) |
| *C07F 15/06* | (2006.01) |
| *C07F 5/02* | (2006.01) |
| *C07F 1/08* | (2006.01) |

(52) U.S. Cl.
USPC .................. 71/31; 71/DIG. 2; 556/7; 556/45; 556/46; 556/57; 556/58; 556/110; 556/112; 556/118; 556/121; 556/138; 556/140

(58) Field of Classification Search
USPC ....... 71/11–63, DIG. 2; 556/139, 119, 57, 45, 556/7, 46, 58, 110, 112, 118, 121, 138, 140
See application file for complete search history.

(56) References Cited

U.S. PATENT DOCUMENTS

| | | | |
|---|---|---|---|
| 5,366,533 A | 11/1994 | Behel, Jr. | |
| 5,632,799 A * | 5/1997 | Behel et al. | ........................ 71/63 |

(Continued)

FOREIGN PATENT DOCUMENTS

| | | | |
|---|---|---|---|
| CN | 101058521 | * | 10/2007 |
| PL | 184745 | * | 12/2002 |
| WO | WO 02/059063 A1 | | 8/2002 |

OTHER PUBLICATIONS

Thomas G. Schlegel et al, "Rates of Foliar Penetration of Chelated Fe (III): Role of Light, Stomata, Species, and Leaf Age", Journal of Agricultural and Food Chemistry (2006), 54 (18), 6809-6813.*

(Continued)

*Primary Examiner* — Wayne Langel
(74) *Attorney, Agent, or Firm* — Hamre, Schumann, Mueller & Larson, P.C.

(57) ABSTRACT

Novel metal complexes useful in the area of agriculture, notably as agents for treating metal deficiency. The novel metal complexes comprise at least one metal selected from the metal trace elements essential for the development of plants, at least one first ligand selected from the lignosulfonates, and derivatives thereof, and at least one second ligand selected from the multidentate organic ligands.

13 Claims, 3 Drawing Sheets

(56) References Cited

U.S. PATENT DOCUMENTS 7,695,541 B1 * 4/2010 Frizzell et al. .................. 71/11
2008/0221314 A1 9/2008 Freire et al.

OTHER PUBLICATIONS

Weglarz et al., "Method of obtaining fertilizing agent containing bioavailable iron," Database Caplus, Online, XP-002534019, 2002.

Anonymous, "Specimen label Brexil FR 10% Iron," Online, XP-002534017, 2002.

Micromix International Ltd., "New company to nourish world crops," International Pest Control, vol. 46, No. 3, pp. 155-156, 2007.

Piaggesi et al., "Measurements of Microelement Content in Pear Leaves as a Consequence of Foliar Sprays with Different Chelates," ACTA Horticulturae, pp. 259-266, 2002.

* cited by examiner

METAL COMPLEXES; USE THEREOF FOR THE PREPARATION OF COMPOSITIONS FOR AGRICULTURAL USE

The present invention relates, to novel metal complexes, and use thereof for the preparation of compositions for agricultural use notably intended for treating deficiencies of essential metal trace elements in plants.

It is known that trace elements are necessary for the development of plants. Thus, iron, manganese, boron, zinc, molybdenum and copper are regarded as trace elements essential for plants.

Among these elements, iron plays an extremely important role in fundamental biological processes, such as the growth, development, photosynthesis and respiration of plants.

The availability of metal trace elements, and in particular of iron, is reduced in alkaline soils or in those rich in active limestone. In fact, in such conditions, these elements form compounds that are insoluble in water (hydroxides, oxides, carbonates, etc.), which are not available for the plant.

Lack of available metal trace elements in the soil, and in particular lack of iron, can adversely affect the physiology of plants. Thus, iron deficiency, for example, causes a yellowing called iron deficiency chlorosis which notably affects young leaves and affects the production potential.

In order to correct phenomena of deficiencies of metal trace elements observed in crops grown on basic or lime soils, new compounds have been developed, which aim to keep these elements available to the plant.

These are essentially metal complexes or chelates using multidentate ligands, and in particular ethylenediaminetetraacetic acid (EDTA) and ethylenediamine-dihydroxyphenylacetic acid (EDDHA).

Thus, iron chelate of EDDHA is widely used for preventing and correcting iron deficiency chlorosis on account of its great stability in an alkaline medium (pH between 7 and 10).

However, these known metal chelates have two major drawbacks:
- from the nutritional standpoint, absorption of these organic chelates by the plant can have an adverse effect on the characteristics of the fruits or vegetables cultivated and can be dangerous to the consumer's health;
- from the environmental standpoint, because of their low biodegradability, these metal chelates constitute a source of pollution of soils and water.

The use of metal complexes based on natural organic substances with complexing properties, such as humic substances, lignosulfonates or tannins, has also been proposed. These compounds are far more environment-friendly, because of their natural character, but their efficacy is limited, so that:
- on the one hand, these complexes are generally of low solubility and are unstable in the soil owing to phenomena of flocculation and precipitation that occur in the presence of cations such as calcium in lime soils; and
- on the other hand, these complexes do not allow the preparation of concentrated products owing to phenomena of molecular aggregation.

U.S. Pat. No. 5,366,533 describes a composition comprising a homogeneous powder of an intimate mixture of a by-product of citrus fruits and of an iron compound such as ferrous or ferric sulfate. Said composition is intended to supply nutrients to the plants.

Application WO 02/059063 describes a fertilizing composition that consists of a combination of a calcium salt and a magnesium salt, with an organic substance selected from a structure-forming agent, a chelating-acidifying substance, a nutrient medium or a mixture of these compounds.

Application US 2008/221314 describes metal complexes comprising a metal, a first ligand selected from humic acid and derivatives thereof, and a second ligand selected from multidentate organic molecules. It was found, however, that complexes of this type lead to release of metal that is not optimal for use for the treatment of deficiencies of metal trace elements in plants.

In these conditions, the aim of the present invention is to solve the technical problem consisting of supplying new metal compounds that do not have the drawbacks of the compounds of the prior art, and in particular that have satisfactory stability and solubility for all types of soils, notably basic and limy, that display high efficacy without posing environmental and health problems, and that permit better release of the metal.

In this context, it was, discovered—and this constitutes the basis of the present invention—that it was possible to solve this technical problem satisfactorily on an industrial scale, by means of novel complexes combining a metal and two different types of ligands, one of which is of natural origin.

According to a first aspect, the present invention relates to a metal complex characterized in that it comprises:
- at least one metal selected from the metal trace elements essential for the development of plants;
- at least one first ligand selected from lignosulfonates, as well as the derivatives of these compounds resulting from biological or chemical transformations, for example by oxidation, reduction, or composting;
- at least one second ligand selected from multidentate organic ligands.

Thus, the metal complexes according to the invention can be represented by the following general formula:

$$[\text{ligand 1}]_n\text{-(metal)}_x\text{-[ligand 2]}_m$$

in which n, x and m represent integers depending on the number of bonds or of coordinations formed between the metal and the ligands.

In general:
n can be equal to 1 or 2;
x can be between 1 and 4;
m can be between 1 and 4.

In the complexes that are preferred according to the invention, n, x and m are equal to 1.

The metal of the complexes according to the invention is a metal trace element essential for the development of plants. This metal is advantageously selected from iron, manganese, boron, zinc, molybdenum, nickel, cobalt and copper. The iron compounds constitute a currently preferred class of the complexes according to the invention.

The first ligand of the complexes according to the invention is selected from lignosulfonates, as well as derivatives of these compounds resulting from biological or chemical transformations, for example by oxidation, reduction, or composting.

These products can be in the form of salts with cations, notably in the form of salts of sodium, of potassium or of ammonium.

The lignosulfonates or sulfonated lignins are known by-products in the production of bisulfite wood pulps. They are water-soluble polymers having various molecular weights, generally between 1000 and 140 000 dalton.

Any type of lignosulfonate can be used within the scope of the present invention. However, lignosulfonates derived from firs or from eucalyptus will be preferred.

The first ligand of the complexes according to the invention can moreover be selected from derivatives of lignosulfonates, said derivatives resulting from biological or chemical transformations, for example by oxidation, reduction or composting.

Derivatives resulting from oxidation can be obtained from the aforementioned compounds, either by injection of oxygen or of air in an alkaline medium, or by treatment with an oxidizing agent, for example sodium periodate or potassium permanganate or persulfate.

Derivatives resulting from reduction can be obtained from the aforementioned compounds by treatment with a reducing agent such as Zn metal.

The second ligand of the complexes according to the invention is generally selected from multidentate organic ligands, i.e. that are capable of binding to the metal by at least two sites.

Advantageously, this second ligand is a polycarboxylic acid of low molecular weight.

As examples of polycarboxylic acids of low molecular weight, we may mention here dicarboxylic acids such as oxalic acid, malonic acid, succinic acid, malic acid, glutaric acid and adipic acid; tricarboxylic acids such as citric acid; and aromatic diacids such as phthalic acid or terephthalic acid.

The second ligand can moreover be a multidentate complexing organic compound such as in particular salicylic acid.

It should be noted that the complexes according to the invention can comprise independently:
one or more metal(s);
one or more first ligand(s);
one or more second ligand(s).

The resultant compounds are constituted of mixtures of complexes.

Metal complexes currently preferred a according to the invention comprise:
iron, preferably Fe(III), as metal;
a lignosulfonate, as first ligand; and
citric acid as second ligand.

Various methods can be used for preparing the metal complexes according to the invention.

Thus, a first method, currently preferred, consists of:
in a first stage, forming a complex or chelate between the metal and the second ligand; then
in a second stage, forming the complex according to the invention by mixing the complex/chelate obtained in the first stage with the first ligand.

This second stage can be carried out:
either by adding the complex/chelate (compound of the metal and of the second ligand) in a solution, preferably aqueous, of the first ligand; said addition being performed batchwise in fractions;
or by adding a solution, preferably aqueous, of the first ligand to a solution containing the complex/chelate in solution or aforementioned.

A person skilled in the art will easily determine the conditions for formation of the complexes according to the invention (pH, pressure, temperature, etc.).

In general, the reactions for obtaining the complexes according to the invention will be carried out with continuous stirring in the liquid phase:
at a pH preferably between 7 and 10;
at a temperature preferably between 25 and 45° C.;
preferably at atmospheric pressure;
for a time preferably between 1 hour and 4 hours.

At the end of the reaction, any solid precipitates that have formed are separated by settling, filtration or centrifugation.

A second method of preparation of the complexes according to the invention consists of adding simultaneously, during one and the same stage, the metal, the first ligand and the second ligand in an aqueous solution.

In this case, the pH will be adjusted preferably to a value of about 8 by means of sodium or potassium hydroxide. The various constituents are preferably used in stoichiometric quantities (expressed relative to the complex). After a time of about 4 hours, the species that have precipitated are separated by centrifugation or by filtration. In the course of the reaction, the temperature is preferably between 25 and 50° C. and the pressure is preferably atmospheric pressure.

A third method of preparation of the complexes according to the invention consists of:
in a first stage, preparing a complex between the metal and the first ligand; then
in a second stage, adding the second ligand to the complex thus prepared.

The metal complexes according to the invention notably find application in the area of agriculture, in particular as agents intended for the treatment of metal deficiencies, notably for treating iron deficiency, when the metal of said compound is iron.

Thus, according to a second aspect, the present invention relates to a composition for agricultural use, comprising at least one metal complex as defined previously together with an agriculturally acceptable support or vehicle.

Said composition can be in solid form, for example in the form of powders, granules or tablets; or alternatively in liquid form in a solvent system, notably aqueous.

In general, a composition for agricultural use according to the invention comprises from 1 to 20 wt. % and preferably from 3 to 15 wt. % of metal complex or metal complexes.

Any type of agriculturally acceptable supports, or vehicles can be used for preparing said composition.

Among solid supports that can be used, we may mention clays, such as, in particular, sepiolite, attapulgite or bentonite.

The liquid or solid compositions according to the invention can be used:
by direct application on a soil, on the entire area of the soil or, preferably, localized in the region of the roots of the plants to be treated; or
by application at the level of the leaves and/or of the plants to be treated, by any suitable means of distribution, for example by spraying in the case of a liquid formulation.

These compositions can in addition be introduced in the system for irrigation with water and/or in fertilizer formulations.

In general, the amount of composition to use depends on the nature of the plant to be treated and on the method of administration envisaged.

In general, a composition according to the invention can be used:

- in an amount for supplying 50 to 80 grams of metal complex or metal complexes per seedling for the treatment of fruit trees, for example from 20 to grams per seedling in the case of the grapevine;
- in an amount for supplying from 10 to 100 kilograms, and preferably from 30 to 40 kilograms of metal complex or metal complexes per hectare, in the case of vegetable growing.

A person skilled in the art will know how to adapt the amounts to be used in relation to the method of application selected. In particular, relatively smaller amounts are used when the composition is applied in the region of the roots whereas relatively larger amounts are used when the composition is applied on the entire area of the soil.

These compositions can be used in a single application or in successive applications, for example from 3 to 5 times with intervals of 15 days.

A composition according to the invention can moreover comprise at least one additional compound selected from mineral nutrients and plant biostimulants.

These compositions can also comprise active compounds such as pesticides, fungicides, herbicides, and nematocides.

Among the additional compounds that can be used, we may mention hormones, humic substances, extracts from algae, amino acids, extracts from plants, salicylic acid and precursors or analogs of salicylic acid, nitric oxide and precursors or analogs of nitric oxide, cyclic nucleotides.

According to a third aspect, the present invention relates to the use of a metal complex as defined previously as an agent intended for treating metal deficiency, said metal being that of the complex.

The invention will now be illustrated by the following nonlimiting examples.

In these examples, and unless stated otherwise; the temperature is room temperature and the pressure is atmospheric pressure.

EXAMPLE 1

Preparation of a Lignosulfonate-Fe(III)-Citrate Complex According to the Invention Stage 1:
24.92 kilograms of iron(III) chloride was added to 45 kilograms of water and the mixture was stirred until the iron salt had dissolved completely.

26 kilograms of citric acid was added to this solution and the reaction mixture was stirred until the citric acid had dissolved completely.

A sufficient amount of potassium hydroxide was added to this solution to adjust the pH of the reaction mixture to a value of 8.

A solution of iron citrate containing 7 wt. % of iron was thus obtained.

Stage 2:
35 kilograms of potassium lignosulfonate (obtained from the Lignotech Iberica company) was added to 30 kilograms of water and the reaction mixture was stirred for a sufficient time to obtain a suspension.

35 kilograms of the solution of iron citrate prepared in stage 1 of example 1 was added in portions to this suspension, and the reaction mixture was stirred for a further 5 hours at 40° C.

A suspension containing 2.5 wt. % of iron in the form of lignosulfonate-Fe(III)-citrate complex (45 kg of lignosulfonate-Fe(III)-citrate complex in solution) was thus obtained.

EXAMPLE 2

Preparation of a Lignosulfonate-Fe(III)-Citrate Complex According to the Invention 13 kilograms of solid iron citrate (18 wt. % of Fe obtained from the company Merck or prepared according to the protocol described in example 1) was added to 80 kilograms of an aqueous solution containing 35 kilograms of potassium lignosulfonate.

To the reaction mixture thus constituted, a sufficient amount of potassium hydroxide was added to adjust the pH to a value of 8.

The reaction mixture was stirred with a helicoidal stirrer for a time of (4 h) at a temperature of (25° C.) to obtain a lignosulfonate-Fe(III)-citrate complex.

EXAMPLE 3

Preparation of a Modified Lignosulfonate-Fe(III)-Citrate Complex According to the Invention Stage 1:
A solution of iron citrate (7 wt. % of iron) was prepared following the experimental protocol of stage 1 of example 1.

Stage 2:
Preparation of the Complex According to the invention.
35 kg of potassium lignosulfonate was added to 30 kg of water and the reaction mixture was, stirred for a sufficient time to obtain a suspension.

1 kg of sodium periodate and 0.5 kg of sodium hydroxide were added to this suspension and the reaction mixture was stirred for a further 4 h.

35 kg of the solution of iron citrate prepared in stage 1 was added in portions to this reaction mixture, the pH was adjusted to 8.5 and the reaction mixture was stirred for a further 5 h at 40° C.

A suspension containing 2.5 wt. % of iron was thus obtained in the form of oxidized lignosulfonate-Fe(III)-citrate complex.

Demonstration of the Properties of the Metal Complexes According to the Invention In this experimental section, notably the following three products were used:

Lignosulfonate-Fe(III) Complex Containing 2.5 Wt. % of Iron Complex

This product was prepared by mixing one liter of an aqueous solution containing 33 wt. % of sodium lignosulfonate (obtained from the company Lignotech Iberica) with 182 grams of a solution of iron(III) chloride at 40 wt. % and by adjusting the pH to a value of 8 with sodium hydroxide.

A gel containing 25 wt. % of iron(III) complexed with lignosulfonate was thus obtained.

This gel is partially insoluble in water.

Lignosulfonate-Fe(III)-Citrate Complex Containing 2.5 Wt. % of Complexed Iron

This product, illustrating the invention, was prepared following the experimental protocol of example 1.

Citrate-Fe(III) Complex Containing 7 Wt. % of Complexed Iron

This product was prepared following the experimental protocol of stage 1 of example 1.

A—Evaluation of the Capacity of the Test Compounds for Keeping Iron Soluble in a Soil in the Presence of Calcium Methodology For each product tested, four solutions were prepared containing 20 milligrams of iron per liter and having respectively a pH of 7, 8, 9 and 10 (the pH having been adjusted with sodium hydroxide or hydrochloric acid).

Four similar solutions were prepared, each containing calcium chloride $CaCl_2$ (0.020 M).

After three days, these solutions were filtered through filters with a pore size of 0.045 micrometer and the iron content in the filters was determined by inductively coupled plasma emission optical spectroscopy (ICP-EOS).

The amount of iron remaining in solution in the presence of calcium ions was calculated using the following formula:

$$\% \text{ of iron remaining} = 100 \times \left( \frac{[Fe]_{pHi+Ca}}{[Fe]_{pHi}} \right)$$

in which:

$[Fe]_{pHi+Ca}$ represents the concentration of iron in the filtrate from a solution (containing calcium chloride 0.020 M) with pH equal to i, expressed in milligrams per liter;

$[Fe]_{pHi}$ represents the concentration of iron in the filtrate from a solution not containing calcium with pH equal to i, expressed in milligrams per liter.

Results

Figure 1:
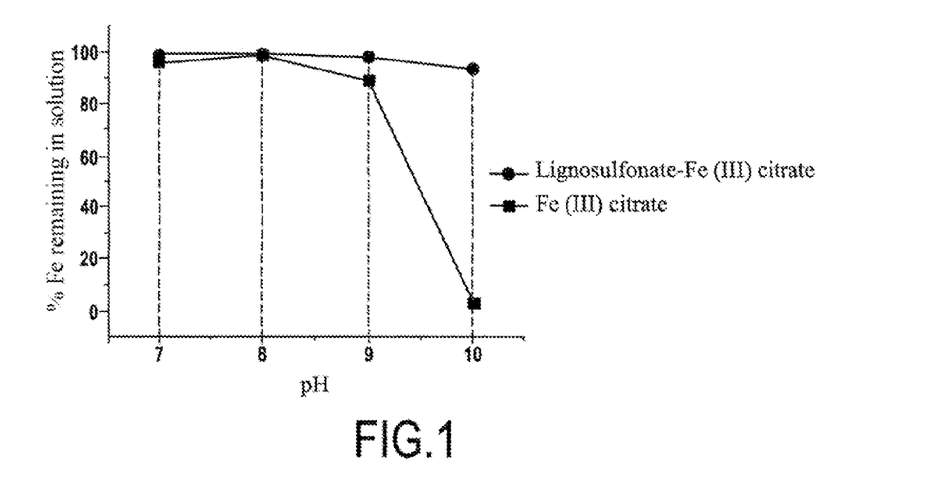
FIG. 1 shows a capacity of the test compounds to retain iron soluble in a soil in the presence of calcium at increasing pH values.

FIG. 1 shows the percentage in iron remaining in solution at the different pH values investigated.

It should be noted that the lignosulfonate-Fe(III) complex was not soluble in the solution containing calcium and therefore does not appear in FIG. 1.

As can be seen from this figure, only the complex of the invention makes it possible to maintain the complexed iron in solution at the different pH values investigated.

It can be seen that the iron complexed with the citrate undergoes precipitation in the range of pH between the values of 9 and 10.

The iron complexed with the lignosulfate alone is not soluble in solution.

These results show the excellent capacity of the complexes according to the invention for supplying iron available for plants cultivated in a lime soil.

B—Determination of the Stability Constant and of the Complexation Capacity of the Test Compounds Methodology Two stock solutions of $Fe(NO_3)_3$ 0.01 M and of lignosulfonate (LG) 1 g $L^{-1}$ in $KNO_3$ 0.1 M at pH 6 were prepared.

Various solutions of LG-Fe(III) single complex were prepared in 0.1 M $KNO_3$ (pH 6), having a constant concentration of lignosulfonate (100 mg $L^{-1}$), and increasing concentrations of Fe(III) (from 0 to 0.00175 M), by slowly adding the stock solution of $Fe(NO_3)_3$ to the solution of lignosulfate.

The stock solution of LG was also used for preparing, according to the experimental protocol of example 1, various solutions of LG-Fe(III)-citrate double complex in 0.1 M $KNO_3$ (pH 6), having a constant concentration of lignosulfonate (10 mg $L^{-1}$), and increasing concentrations of Fe(III) (from 0 to 0.00175 M).

The fluorescence intensity (FI) of each solution tested was measured using a Kontron Instruments SFM 25 luminescence spectrometer controlled by WIND 25 1.50 software (Kontron Instruments Ltd.), using an excitation wavelength of 335 nm, and fixing the emission wavelength at 400 nm (values that correspond to the maximum of the excitation and emission spectrum of LG).

The stability constant of the Fe(III) complexes, and the complexation capacity of said complexes, were determined according to the model described by Ryan and Weber (*Anal. Chem.* 1982, 54, 986-990). The conditional stability constant (K) of formation of a complex between a metal ion and a ligand at constant pH and ionic strength is defined by the equation:

$$K = \frac{[ML]}{[M][L]} \quad (1)$$

where [ML] is the molar concentration of the metal-ligand complex, [M] is the molar concentration of the free metal, and [L] is the molar concentration of the noncomplexed ligands. The conservation of mass for the metal and the ligand is written:

$$C_M = [M] + [ML] \quad (2)$$

$$C_L = [L] + [ML] \quad (3)$$

where $C_M$ is the total concentration of metal ion, and $C_L$ is defined as the equivalent total ligand concentration at the end of titration in terms of molar concentration of metal ion.

The fraction of bound ligand can be expressed by combining equations (1) and (3):

$$v = \frac{[ML]}{C_L} = \frac{K[M]}{1 + K[M]} \quad (4)$$

which, on replacing [M] by means of equation (2), gives:

$$v = \frac{K(C_M - vC_L)}{1 + K(C_M - vC_L)} \quad (5)$$

Moreover, as the ligand passes from the unbound state to the bound state during titration, the quantum efficiency varies linearly according to the equation:

$$v = \frac{I_0 - I}{I_0 - I_{ML}} \quad (6)$$

where I is the total measured fluorescence intensity, $I_0$ is the fluorescence intensity in the absence of metal ion, and $I_{ML}$ is the fluorescence intensity of the complex saturated with metal.

The value of v is found from equation (5):

$$v = \left( \frac{1}{2KC_L} \right) \left( 1 + KC_L + KC_M - \sqrt{(1 + KC_L + KC_M)^2 - 4K^2 C_L C_M} \right) \quad (7)$$

Combining equations (6) and (7), a curve is obtained that represents the measured fluorescence intensities as a function of the total concentration of metal ion ($C_M$):

$$I = I_o + (I_{ML} - I_o)\left(\frac{1}{2KC_L}\right) \quad (8)$$

$$\left(1 + KC_L + KC_M - \sqrt{(1 + KC_L + KC_M)^2 - 4K^2C_LC_M}\right)$$

For each data pair, equation (8) can be solved by nonlinear regression analysis of K, $C_L$ and $I_{ML}$. The Origin 6.1 software (OriginLab Corporation, Northampton, Mass.) was used for the calculations.

Finally, the complexation capacity (CC), defined as the quantity of active binding sites per unit of mass of LG, is calculated according to equation (9):

$$CC = \left(\frac{C_L}{[LG]_{tot}}\right) \quad (9)$$

where $[LG]_{tot}$ is the total concentration of lignosulfonate.
Results

Figure 2A:
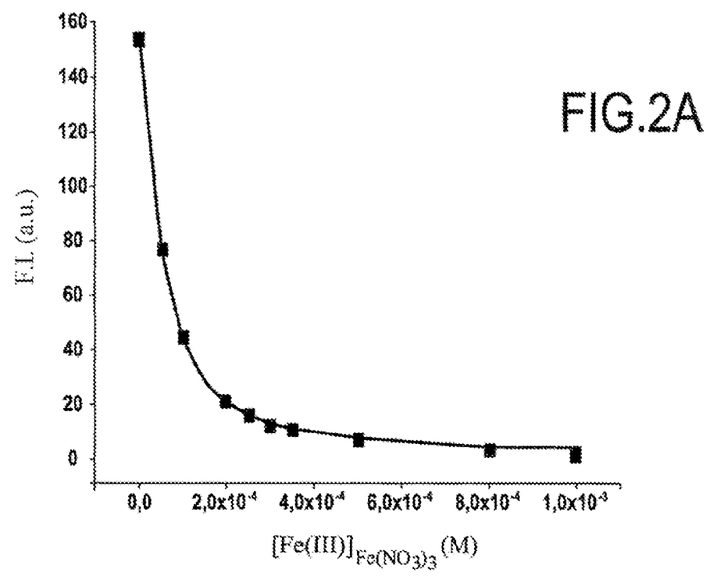
FIG. 2A and FIG. 2B show fluorescence intensity of the test compounds at increasing Fe(III) concentrations.
Figure 2B:
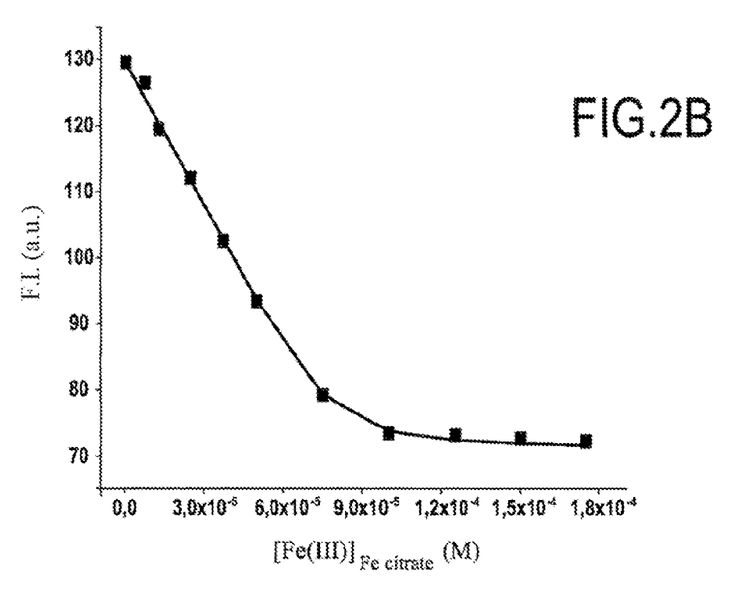

The results thus obtained are presented in the table shown below, and are represented in FIGS. 2A and 2B, in which $[Fe(III)]_{Fe(NO3)_3}$ represents the single LG-Fe(III) complex and $[Fe(III°)]_{Fe\text{-}citrate}$ represents the double LG-Fe(III)-citrate complex.

| Sample | R | log K | $CC_{Fe}$ (mmol/g LG) |
|---|---|---|---|
| $[Fe(III)]_{Fe(NO3)_3}$ | 0.999 | 4.6 ± 0.1 | 0.5 ± 0.1 |
| $[Fe(III°)]_{Fe\text{-}citrate}$ | 0.998 | 5.4 ± 0.1 | 8.0 ± 0.4 |

As can be seen, the stability constant of the LG-Fe(III)-citrate complex (log K=5.4) is about 6 times higher than that of the LG-Fe(III) complex (log K=4.6). Moreover, the complexation capacity of the LG-Fe(III)-citrate complex (8.0 mmol/g LG) is 16 times higher than that of the LG-Fe(III) complex (0.5 mmol/g LG).

These results therefore show the superiority of the double complexes according to the invention relative to the corresponding single complex, in that the double complexes can bind a larger amount of metal, with increased stability.

C—Investigation In Vivo

This study evaluated the ability of the test compounds to supply iron in available form for cucumber seedlings grown in a lime soil.

Methodology

Cucumber seeds (*Cucumis sativus* L. cv. *Ashley*) were placed in polyethylene pots containing perlite moistened with a solution of calcium sulfate $CaSO_4$ (1 mM). The pots were placed in a germinating chamber at 24° C. and 85% relative humidity for one week, in the dark for the first 5 days and then with a photoperiod of 12/12 h day/night.

The seedlings thus obtained were transferred to the individual cells of a polyethylene box.

Each cell had been filled beforehand with perlite impregnated with a nutrient solution (pH=6) containing:
 1 µM Fe-EDDHA;
 2 mM $Ca(NO_3)_2$;
 0.75 mM $K_2SO_4$;
 0.65 mM $MgSO_4$;
 0.5 mM $KH_2PO_4$;
 50 µM KCl;
 10 µM $MnS_4$;
 0.5 µM $CuSO_4$;
 0.5 µM $ZnSO_4$; and
 0.35 µM $NaMoO_4$.

The seedlings were cultivated in a growing chamber (luminous intensity: 250 mol m$^{-2}$ s$^{-1}$) with a photoperiod of 15/9 h day/night, a mean temperature of 28/21° C. (day/night) and a relative humidity of 70 to 75.

After development of the first leaf, thirty seedlings were transferred to opaque plastic pots of 1 liter, each containing 600 grams of a lime soil and 40 grams of perlite.

The pots were watered, adding 230 milliliters of a solution of $Ca(NO_3)_2$ (9 mM) and 10 milliliters of a solution of $K_2HPO_4$ (0.96 M).

Three products were tested:
 the Fe(III)-citrate and lignosulfonate-Fe(III)-citrate complexes mentioned previously
 $Fe(SO_4)$ (obtained from the company PANREAC SA)

The Fe-lignosulfonate complex was not tested in this case, since this product is not water-soluble.

Five identical samples of each product were tested, at two different doses corresponding to an iron supply of 2 and 5 milligrams per kilogram of soil.

Each seedling was placed in a forcing chamber (photoperiod: 15/9 h day/night; 70-85% relative humidity; temperature 15° C./24° C.) and was watered twice a week with deionized water up to the total irrigation capacity (240 milliliters).

After twenty days, the seedlings were harvested and the leaves were stove-dried at 40° C. for 72 hours.

The dried leaves were ground in a titanium grinding mill. 0.5 g of ground product was digested in Teflon pots of the "digestion bomb" type with 2 ml of 30% hydrogen peroxide and 8 ml of 65% nitric acid. Digestion was carried out for 30 minutes at 200° C. in an Ethos microwave from Millestone. The digestions are calibrated at 25 ml with distilled water of MilliQ quality.

The total iron content of the leaves was determined by ICP-EOS.
Results

Figure 3:
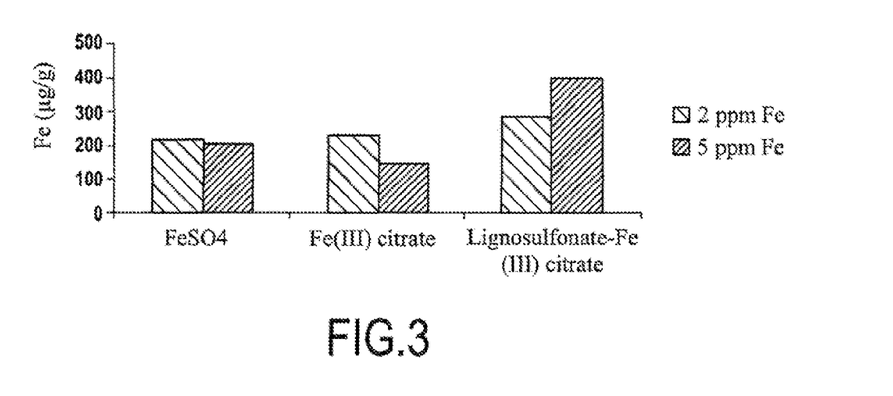
FIG. 3 shows an ability of the test compounds to supply iron in an available form to cucumber seedlings.

The results thus obtained are presented in FIG. 3.

As can be seen from this figure, the complexes according to the invention have much higher efficacy than that of iron sulfate and of iron citrate in terms of concentration of iron in the leaves of the treated plants.

This effect is particularly significant at a dose of 5 mg/kg of iron in the soil.

D—Investigation In Vivo

This investigation evaluated the ability of the test compounds to supply iron in available form for peach trees.

The experiment was carried out on peach trees (*Prunus persica*) aged 6 years, planted in an experimental plot with lime soil, with a clay loam texture, high pH (8.5), and a low iron content (5.8 mg per kg of soil).

Two products were tested:
 the lignosulfonate-Fe(III)-citrate complex containing 2.5 wt. % of iron complex, obtained according to the experimental protocol of example 1,
 a humic acid-Fe(III)-citrate complex containing 3.8 wt. % of complexed iron, obtained according to the experimental protocol of example 1 of application S 2008/221314.

Each product was applied twice by micro-irrigation, with an interval of 18 days, on six sets of two trees selected randomly in the plot.

Thirty leaves per tree were taken at 20 days, 41 days, 61 days and 76 days after the first application; these leaves were stove-dried at 40° C. for 72 hours, then ground in a titanium grinding mill.

The total iron content was determined starting from 0.5 g of ground product digested in Teflon pots of the "digestion bomb" type with 2 ml of 30% hydrogen peroxide and 8 ml of 65% nitric acid. Digestion was carried out for 30 minutes at 200° C. in an Ethos microwave from Millestone. The digestions are calibrated at 25 ml with distilled water of MilliQ quality, and then analyzed by ICP-EOS.

The content of iron extractable with HCl was determined starting from 2 g of ground product, transferred to a tube, to which 20 ml of 1N HCl was added. The tube were stirred for 4 h, centrifuged for 10 min at 12000 g, and the supernatant was filtered on filter paper. The iron content of the filtrate was analyzed by ICP-EOS.

Results

Figure 4A:
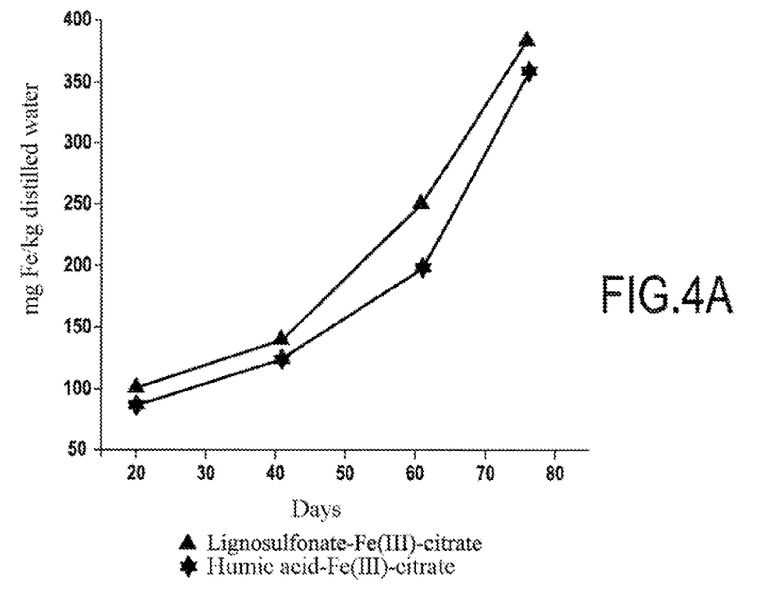
FIG. 4A and FIG. 4B show an ability of the test compounds to supply iron in an available form to peach trees.
Figure 4B:
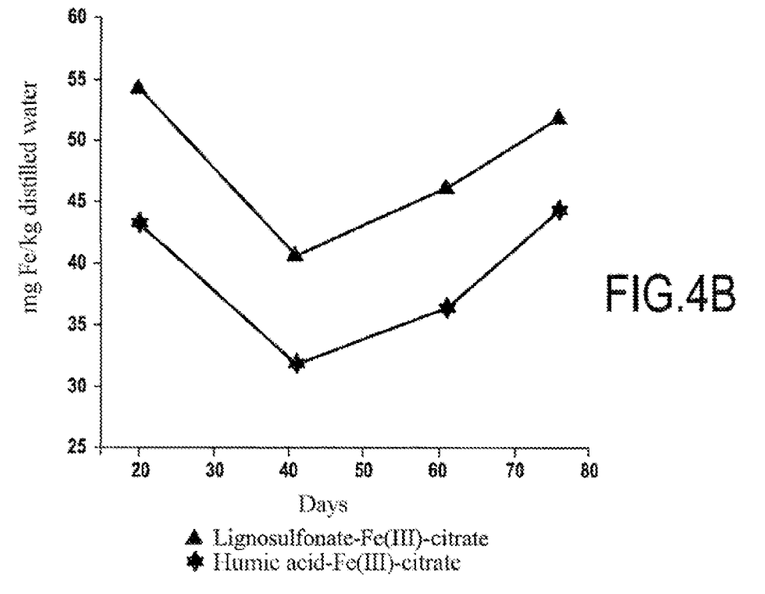

The results thus obtained are presented in FIGS. 4A and 4B.

As can be seen from these figures, the total iron content (FIG. 4A) and content of iron extractable with HCl (FIG. 4B) in the peach tree leaves treated with the double complex based on lignosulfonate is greater than that of the leaves treated with the double complex based on humic acid.

The invention claimed is:

1. A metal complex, represented by a following formula:

$$[\text{ligand 1}]_n\text{-(metal)}_x\text{-[ligand 2]}_m,$$

wherein the metal is selected from the group consisting of iron, manganese, boron, zinc, molybdenum, nickel, cobalt, and copper, the ligand 1 is a lignosulfonate, and the ligand 2 is selected from the group consisting of citric acid, oxalic acid, malonic acid, succinic acid, malic acid, glutaric acid, phthalic acid, terephthalic acid, adipic acid, and salicylic acid, and n, x, and m are positive integers that satisfy requirements imposed by a number of bonds or of coordinations formed between the metal and the ligand 1 and between the metal and the ligand 2.

2. The complex as claimed in claim 1, wherein said metal is iron, and said ligand 2 is citric acid.

3. A composition for agricultural use, wherein the composition comprises at least one metal complex according to claim 1 together with an agriculturally acceptable support or vehicle.

4. The composition as claimed in claim 3, wherein the composition comprises the at least one metal complex in an amount from 1 to 20 wt. %.

5. The composition as claimed in claim 3, wherein the composition further comprises at least one additional compound selected from the group consisting of mineral nutrients and plant biostimulants.

6. The composition as claimed in claim 3, wherein the composition is in a solid form or in a liquid form.

7. The complex as claimed in claim 2, wherein the iron is in a form of Fe(III).

8. The composition as claimed in claim 4, which comprises the at least one metal complex in an amount from 3 to 15 wt. %.

9. The composition as claimed in claim 6, wherein the composition is in the solid form, which is a powder, a granule, or a tablet.

10. A metal complex represented by a following formula:

$$[\text{ligand 1}]_n\text{-(metal)}_x\text{-[ligand 2]}_m$$

wherein the metal is selected from the group consisting of iron, manganese, boron, zinc, molybdenum, nickel, cobalt and copper;

the ligand 1 is a lignosulfonate; and the ligand 2 is selected from the group consisting of citric acid, oxalic acid, malonic acid, succinic acid, malic acid, glutaric acid, phthalic acid, terephthalic acid, adipic acid, and salicylic acid, and wherein n is 1 or 2, x is 1, 2, 3 or 4, and m is 1, 2, 3 or 4.

11. The complex as claimed in claim 10, wherein n, x, and m are each 1.

12. A method of treating metal deficiency of a plant or growing a plant, said metal being selected from the group consisting of iron, manganese, boron, zinc, molybdenum, nickel, cobalt, and copper, wherein the method comprises a step of applying a metal in a form of the metal complex as claimed in claim 1 to the plant.

13. The method as claimed in claim 12, wherein said metal complex is applied in an amount from 50 to 80 grams per seedling to fruit trees for the treatment or in an amount from 30 to 40 kilograms per hectare to a vegetable for the growing.

* * * * *

UNITED STATES PATENT AND TRADEMARK OFFICE
CERTIFICATE OF CORRECTION

| | | |
|---|---|---|
| PATENT NO. | : 8,652,231 B2 | Page 1 of 1 |
| APPLICATION NO. | : 13/124303 | |
| DATED | : February 18, 2014 | |
| INVENTOR(S) | : Fuentes et al. | |

It is certified that error appears in the above-identified patent and that said Letters Patent is hereby corrected as shown below:

TITLE PAGE:

Item (73) Assignee: Timac Argo International, Saint-Malo (FR) should be

-- TIMAC AGRO INTERNATIONAL, Saint-Malo (FR) --

Signed and Sealed this
Sixteenth Day of December, 2014

Michelle K. Lee
*Deputy Director of the United States Patent and Trademark Office*